United States Patent [19]

Woltersdorf, Jr. et al.

[11] 4,224,447

[45] Sep. 23, 1980

[54] NOVEL PYRAZINECARBOXAMIDES AND PROCESSES FOR PREPARING SAME

[75] Inventors: Otto W. Woltersdorf, Jr., Chalfont; Susan J. deSolms, Norristown, both of Pa.

[73] Assignee: Merck & Co., Inc., Rahway, N.J.

[21] Appl. No.: 24,294

[22] Filed: Mar. 27, 1979

[51] Int. Cl.² .......................................... C07D 417/12
[52] U.S. Cl. .................................................. 544/405
[58] Field of Search ......................................... 544/405

[56] References Cited

U.S. PATENT DOCUMENTS 3,313,813   4/1967   Cragoe, Jr. ......................... 544/405

*Primary Examiner*—Jose Tovar
*Attorney, Agent, or Firm*—Michael C. Sudol, Jr.; Harry E. Westlake, Jr.

[57] ABSTRACT

The case involves novel pyrazinecarboxamide compounds and processes for preparing same. The pyrazinecarboxamides are eukalemic agents possessing diuretic and natriuretic properties.

6 Claims, No Drawings

NOVEL PYRAZINECARBOXAMIDES AND PROCESSES FOR PREPARING SAME

SUMMARY OF THE INVENTION

The instant case relates to a novel process for preparing pyrazinecarboxamide compounds of Formula I below.

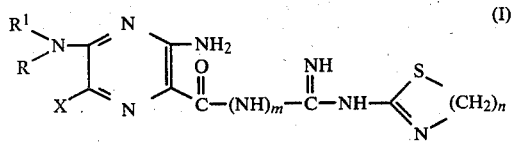

wherein
R and $R^1$ are hydrogen,
  lower alkyl having from 1 to 5 carbon atoms such as methyl, ethyl, isopropyl, n-butyl, n-pentyl, cycloalkyl having from 3 to 6 carbon atoms such as cyclopropyl, cyclopentyl and cyclohexyl;
  lower alkenyl having from 2 to 5 carbon atoms such as allyl;
  lower alkynyl having from 2 to 5 carbon atoms such as propargyl or aralkyl, particularly ar-lower ($C_{1-3}$) alkyl such as benzyl;
X is halogen such as chloro, bromo, fluoro or iodo;
n is an integer selected from 2 or 3, and
m is an integer selected from 1 or 2.

In addition to the novel process for preparing the compounds shown above as Formula (I), and which is described above, our invention also relates to novel compounds of Formula (I) wherein m is 2 and R, $R^1$, X and n are as above defined.

The preferred novel compounds of this invention are those compounds of Formula I wherein
R is hydrogen,
$R^1$ is hydrogen, or lower alkyl having from 1 to 3 carbon atoms;
X is chloro,
m is 2, and
n is 2 or 3.

The novel process of this invention for preparing compounds of Formula I and the preferred compounds can be depicted by the following equation:

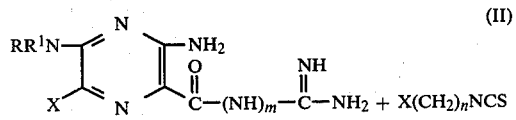

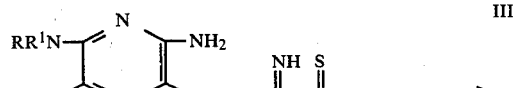

wherein R, $R^1$, X, n and m are as defined in Formula I.

This involves a reaction of a pyrazinoylguanidine or pyrazinamidoguanidine with a haloalkylisothiocyanate forming as an intermediate a compound of structure (III), which may be isolated, or the reaction may be continued for a longer time causing the elimination of HX thus forming the heterocyclic substituent. The reaction is usually run at a temperature from about room temperature to 100° C. The reaction time is usually from one to 48 hours and the reactants are in mole to mole ratios. None of these reaction conditions are critical and they can be varied by those skilled in the art. The desired product is then isolated from the reaction mixture by procedures well known in the art such as by filtration of the precipitated desired product or its salt, washing it with water and drying it.

The starting materials used in the processes described above are shown in and disclosed in U.S. Pat. No. 3,313,813 (Compound II) or are commercially available (III).

The compounds as shown by Formula (I) and the preferred compounds discussed above are useful because they possess diuretic and natriuretic properties. In addition, they are useful eukalemic saluretics, in other words, the compounds of the instant case cause neither loss or abnormal retention of potassium ions. Thus, the compounds of this invention maintain the excretion of potassium at approximately normal levels while causing an increased renal elimination of sodium ions and water which is the desirable characteristic of the diuretic.

Since the compounds of the instant invention are thus eukalemic saluretic agents they constitute single entities which are useful for the treatment of edema and hypertension and other diseases or conditions known to be responsive to this therapy.

The products of this invention can be administered to patients (both human and animal) in the form of pills, tablets, capsules, elixirs, injectable preparations and the like. They can be administered either orally or parentally or any other feasible method as known to those skilled in the art such as intravenously or in the form of suppositories and the like.

The type of formulation to be administered can be comprised of one or more of the compounds of this invention as the only essential active ingredient of the pharmaceutical formulation. The formulations are merely combinations of the active ingredient mentioned with pharmaceutically inert carriers and the like.

The compounds of this invention are advantageously administered at a dosage range of from about 5 mg. to about one gram per day or a somewhat higher or lower dosage at the physician's discretion, preferably in subdivided amounts on a 2 to 4 times a day regimen and most preferably at a dosage range from 10 to 500 mg. per day. It will be realized by those skilled in the art that the dosage range for any particular patient (animal or human) will depend upon the severity of the disease treated, weight of the patient and any other condition which the physician or other person skilled in the art will take account of.

The following examples are included to illustrate the preparation of compounds of this invention and also to illustrate the preparation of a representative dosage form.

EXAMPLE 1

Preparation of 3,5-Diamino-6-chloro-N-[(2-thiazolinylamino)aminomethylene]2-pyrazinecarboxamide 2-Chloroethylisothiocyanate (670 mg., 0.0055 mole) is added to a warm (40° C.) solution of N-amidino 3,5-diamino-6-chloro-2-pyrazinecarboxamide (1.15 g., 0.005 mole) in DMF (30 ml.) with stirring. After 2 hours, the solid precipitate is collected, washed with H₂0 and dried to give 3,5-diamino-6-chloro-N-[(2-thiazolinylamino)aminomethylene]-2-pyrazinecarboxamide., m.p. 252°-254° C.

EXAMPLE 2

Preparation of 3,5-Diamino-6-chloro-N-{[(2-thiazolinylamino)iminomethyl]amino}-2-pyrazinecarboxamide 2-Chloroethylisothiocyanate (1.34 g., 0.011 mole) is added to a warm (40° C.) solution of N-guanidino-3,5-diamino-6-chloro-2-pyrazinomide (2.44 g., 0.01 mole) in DMF (60 ml.) with stirring. After 3 hrs. the solid precipitate is collected, washed with H₂0 and dried to give 3,5-diamino-6-chloro-N-[(2-thiazolinylamino)iminomethylamino]-2-pyrazinecarboxamide,.

EXAMPLE 3

Preparation of 3,5-Diamino-6-chloro-N-{[2-(4,5-dihydro)-1,3-thiazinylamino]aminomethylene}-2-pyrazinecarboxamide hemihydrate 3-Chloropropylisothiocyanate (1.49 g., 0.011 mole) is added to a warm (40° C.) solution of N-amidino-3,5-diamino-6-chloro-2-pyrazinecarboxamide (2.29 g., 0.01 mole) in DMF (60 ml.) with stirring. After 3 hours the solid precipitate is collected, washed with H₂O and dried to give 3,5-diamino-6-chloro-N-{[2-(4,5-dihydro)-1,3-thiazinylamino]aminomethylene}-2-pyrazinecarboxamide hemihydrate, m.p. 214°-17° C.

EXAMPLE 4

| Compressed Tablet containing 50 mg. of active ingredient | |
|---|---|
| | Per Tablet, Mg. |
| 3,5-diamino-6-chloro-N-[(2-thiazolinylamino)amino-methylene]-2-pyrazinecarboxamide | 50 |
| Calcium phosphate dibasic | 200 |
| Ethyl cellulose (as 5% solution in ethanol) | 5 |
| Unmixed granulation | 255 |
| Add: | |
| Starch, corn | 14 |
| Magnesium stearate | 1 |
| | 270 |

Directions: Mix the active ingredient above and calcium phosphate and reduce to a No. 60 mesh powder. Granulate with Ethocel in alcohol and pass the wet granulation through a No. 10 screen. Dry the granulation at 110° F. for 12-18 hours. Dry grind to a No. 20 mesh. Incorporate the "adds" and compress into tablets each weighing 270 mg.

What is claimed is:

1. A compound of the formula:

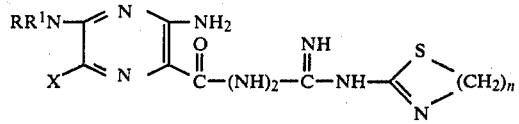

wherein
R and $R^1$ are hydrogen
lower alkyl having from 1 to 5 carbon atoms,
cycloalkyl having from 3 to 6 carbon atoms,
lower alkenyl having from 2 to 5 carbon atoms;
lower alkynyl having from 2 to 5 carbon atoms, or
aralkyl wherein the alkyl group has 1 to 3 carbon atoms;
X is halo;
n is an integer selected from 2 or 3.

2. A compound of the formula:

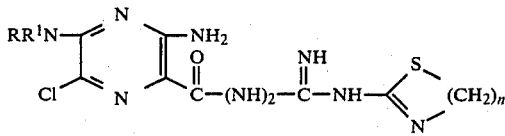

wherein
R is hydrogen;
$R^1$ is hydrogen or lower alkyl having from 1 to 3 carbon atoms; and
n is an integer selected from 2 or 3.

3. A compound of claim 2 wherein R and $R^1$ are hydrogen and n is 2.

4. A process for preparing compounds of the formula:

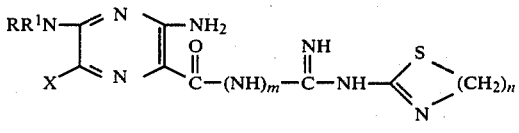

wherein
R and $R^1$ are hydrogen,
lower alkyl having from 1 to 5 carbon atoms,
cycloalkyl having from 3 to 6 carbon atoms,
lower alkenyl having from 2 to 5 carbon atoms;
lower alkynyl having from 2 to 5 carbon atoms, or
aralkyl wherein the alkyl group has 1 to 3 carbon atoms;
X is halo;
n is an integer selected from 2 or 3, and
m is 1 or 2
which comprises reacting a pyrazinoylguanidine or pyrazinecarboxamidoguanidine of the formula:

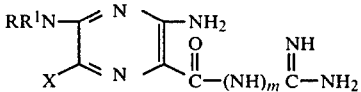

with a substituted isothiocyanate of the formula:

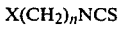

wherein R, $R^1$, X, Y, n and m are as defined above followed by cyclization to produce the desired product.

5. A process for preparing compounds of the formula:

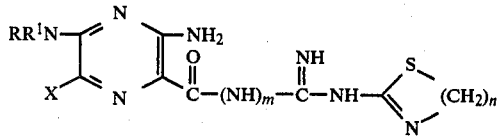

wherein
 R is hydrogen;
 $R^1$ is hydrogen or lower alkyl having from 1 to 3 carbon atoms;
 n is an integer selected from 2 or 3;
 M = 1 or 2;
which comprises reacting a pyrazinoylguanidine or pyrazine carboxamidoguanidine of the formula:

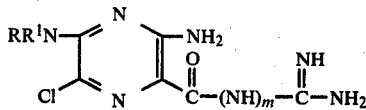

with a substituted isothiocyanate of the formula:

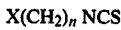 NCS wherein R, $R^1$, X, n and m are as above defined followed by cyclization to produce the desired product.

6. A process of claim 5 wherein the pyrazinamidoguanidine is N-guanidino-3,5-diamino-6-chloro-2-pyrazinecarboxamide and the isothiocyanate is 2-chloroethylisothiocyanate which yields 3,5-diamino-6-chloro-N-{[(2-thiazolinylamino)iminomethyl]-amino}-2-pyrazinecarboxamide.

* * * * *